United States Patent [19]

Burough et al.

[11] Patent Number: 4,709,150
[45] Date of Patent: Nov. 24, 1987

[54] METHOD AND APPARATUS FOR DETECTING GAS

[76] Inventors: Irvin G. Burough, 1656 Camino Verde, Walnut Creek, Calif. 94596; Robert O. Pellissier, 3990 Salvador Ct., Pleasanton, Calif. 94566; Kenneth W. Johnson, 4078 Laguna Way, Palo Alto, Calif. 94306

[21] Appl. No.: 840,929

[22] Filed: Mar. 18, 1986

[51] Int. Cl.⁴ ............................................. G01N 21/35
[52] U.S. Cl. .................................... 250/338; 250/343; 356/437
[58] Field of Search ................ 256/338 GA, 373, 435, 256/351, 343, 436; 356/438, 437, 440

[56] References Cited

U.S. PATENT DOCUMENTS

| | | | |
|---|---|---|---|
| 3,529,152 | 9/1970 | Strange et al. | 250/345 |
| 3,790,797 | 2/1974 | Sternberg et al. | 250/345 |
| 3,826,918 | 7/1974 | Van Der Koogh et al. | 250/343 |
| 3,860,818 | 1/1975 | Stalder et al. | 356/437 |
| 4,323,777 | 4/1982 | Baskins | 250/343 |
| 4,437,005 | 3/1984 | Ophoff et al. | 250/351 |

FOREIGN PATENT DOCUMENTS

| | | | |
|---|---|---|---|
| 3441280 | 5/1985 | Fed. Rep. of Germany | 250/343 |
| 5684 | 1/1978 | Japan | 356/437 |

*Primary Examiner*—Carolyn E. Fields
*Attorney, Agent, or Firm*—Glen R. Grunewald; Lampel Thomas R.

[57] ABSTRACT

An analyzer to detect a specific gas in the atmosphere by infrared absorption, having a porous tube surrounding an enclosed column of air, the porous tube having an average pore size to permit gas to diffuse through it quickly, and having within the tube an infrared source, an infrared detector and an optical filter that passes those portions of the infrared spectrum most strongly absorbed by the gas, the analyzer having a time base generator to pulse the infrared source and electronic means to measure the maximum and minimum signals from the detector and a meter to indicate the difference between the maximum and minimum as a measure of the amount of the gas in the column of air.

19 Claims, 2 Drawing Figures

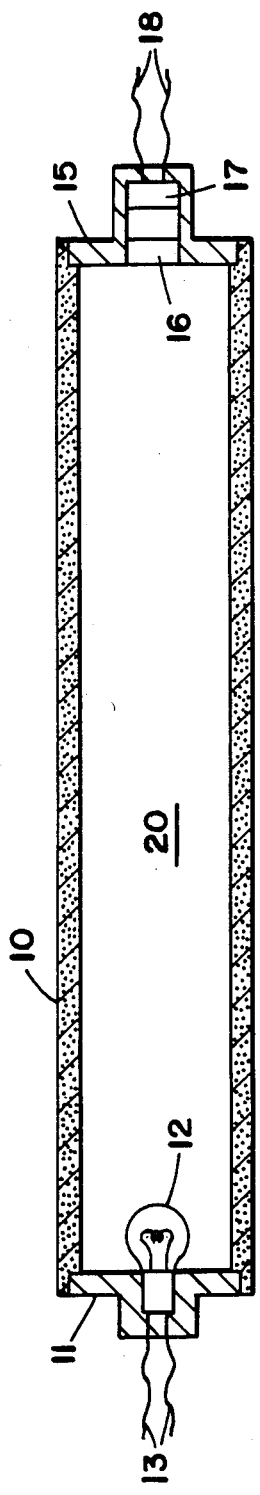
FIG_1
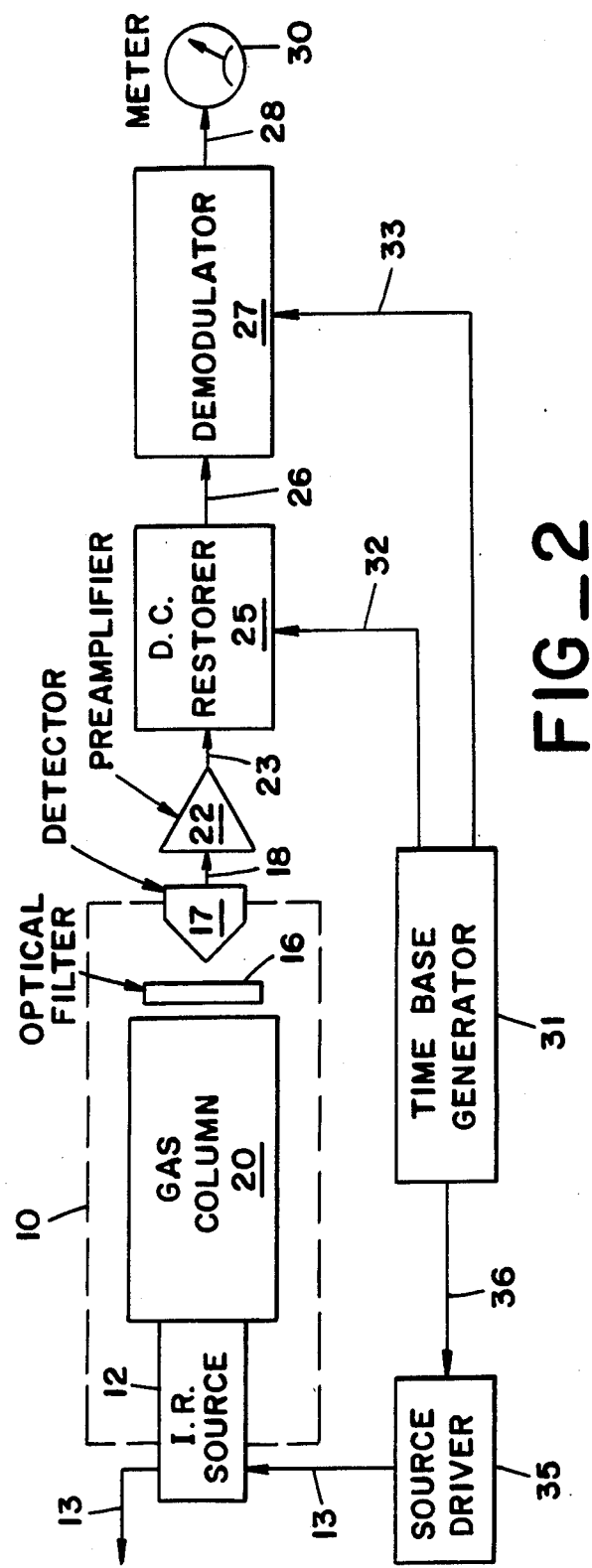
FIG_2

METHOD AND APPARATUS FOR DETECTING GAS

FIELD OF THE INVENTION

This invention relates to detectors to measure the presence of and the amount of particular gases in air.

BACKGROUND OF THE INVENTION

To regulate the quality of air in occupied spaces it is necessary to insure that enough fresh air in introduced into the spaces to keep a comfortable and healthful atmosphere. For example, in office buildings air is circulated and recirculated through heating and cooling systems. Ultimately contaminants build up in the air and it becomes unhealthful to breathe as well as having a general feeling of staleness. Respiration introduces water vapor and carbon dioxide into the air and occupants of rooms cause other such things as perfume, cosmetics, perspiration and solvents to enter the atmosphere and contribute to the sense of air staleness.

Government regulations frequently require an amount of fresh air to be introduced into a recirculating air system for each cycle of recirculation. This approach to maintain air fresh is inadequate. It is approximate, it is difficult to effect because the quantity of recirculating air and the quantity of fresh air are difficult to monitor and because it does not take into account differences in population density, for example between an executive office and a crowded conference room.

Although it is difficult to monitor each of the contaminants that contribute to air staleness, one good measure of population density in an enclosed room that correlates closely with all of those contaminants is the carbon dioxide level of the air. It is a good indication of population because it is generated by respiration. Carbon dioxide level also correlates closely with carbon monoxide level in environments where internal combustion engines are used in enclosed spaces, for example in a garage or an underground mine.

In some industries it is desirable to monitor other gases. Chemical plants may monitor volatile material such as benzene and mines must monitor the methane level of the atmosphere both to maintain a healthy atmosphere and to avoid explosions.

Devices useful for monitoring the air desirably are inexpensive and small enough to be portable.

Many devices presently exist to monitor air for the presence for contaminant gases. Many of these devices function on the basis of the ability of contaminant gases to absorb infrared radiation. These devices enclose a column of gas to be monitored and place an infrared source at one end of the column and an infrared detector at the other and then introduce the gas to be monitored into the column. Infrared monitoring is desirable because specific narrow frequency bands of infrared radiation are very strongly absorbed by specific gases so the presence of those gases can be detected by measuring the absorption of infrared energy in those narrow bands. For example, carbon dioxide very strongly absorbs that portion of the infrared spectrum between 4.2 and 4.4 microns in wave length while methane strongly absorbs the portion between 3.1 and 3.6 microns in the wave length.

In many devices the quantity of a contaminant gas is measured by comparing the absorption in a column of gas known to contain none of the contaminant with the absorption of a column of the gas being analyzed. The gas being analyzed is pumped through a tube having an infrared source at one end and a detector at the other with appropriate optical filters between the source and the detector to pass only the narrow band most strongly absorbed by the contaminant for which the analysis is performed. To create an alternating current effect which is desirable from a signal processing standpoint, a chopper is positioned between the infrared source and the detector. After suitable calibration of the instruments, the difference between the amounts of infrared absorbed in the reference column and in the analysis column can be correlated to the concentration of the contaminant in the analysis column. Devices of this type are disclosed in U.S. Pat. Nos. 3,529,152 and 3,790,797.

The devices described above require moving choppers which operate in a free air optical path between the source of infrared and the gas column. This free air path may contribute to inaccuracies in the analysis because there is no control over a contaminant level in that path. The problem is particularly acute if sampling of the air to be monitored is remote from the position of the infrared source. The mechanical chopper also requires moving parts which are susceptible to breakage, which are noisy, which require maintenance, and which must be made explosion proof if used, for example, to monitor the methane level in a mine. In addition, air passed through the columns must be pumped and filtered so dust does not affect the absorption of infrared and such systems require moving parts to pump the air and filter maintenance to insure that it is clean and flowing at a uniform rate.

SUMMARY OF THE INVENTION

The device of this invention greatly mitigates or obviates the problems mentioned above. The device of this invention is a small, inexpensive gas detector which can be battery powered, transportable or fixed and which requires no moving parts in order to monitor the amount of any gas that can be detected by absorption of a narrow band of infrared or other radiation. The device is particularly useful for monitoring carbon dioxide and will be described largely with respect to carbon dioxide monitoring even though it may also be employed to monitor other gases.

The device includes an analysis cell having enclosed within it a radiation source, preferably an infrared source, an optical filter and a detector for the radiation. The cell is formed of a hollow porous element that is elongated so that the source is maintained at one end of it and the detector is maintained at the other. The porous element preferably is cylindrical and its porosity is regulated so that air can diffuse into and out of it readily. A preferred porous material is porous plastic because most porous plastics are hydrophobic and prevent water from entering the gas cell, although other porous materials such as sintered ceramic or sintered metal such as stainless steel or bronze may be used effectively. Sintered metal is the preferred material when the device is used in an explosive atmosphere, such as to monitor methane in a mine, because the sintered metal shell is a flame barrier that will prevent flame propagation from within the sintered housing.

The radiation source is electronically pulsed between on and off positions so that the detector receives intermittent exposure to radiation thereby producing an alternating current response that is easy to relate to concentration as will be described below.

BRIEF DESCRIPTION OF THE DRAWINGS

FIG. 1 is a cross section of a cell useful in the device of this invention.

FIG. 2 is a schematic diagram of a system embodying this invention.

DETAILED DESCRIPTION OF THE INVENTION

FIG. 1 illustrates a cross section of a gas cell embodying the invention. This cell includes a porous cylindrical element 10 having a hollow interior in which a gas column 20 may be maintained. The cell includes an end cap 11 adapted to mount a source of radiant energy 12 which may be an incandescent lamp having a tungsten filament to produce infrared radiation. The selection of the source will depend on the wave length of the radiation required by the gas to be measured. For example, although carbon dioxide and methane are best detected with infrared, oxygen, ozone and nitrogen oxides can be detected in portions of the ultraviolet spectrum. Other infrared sources may be used such as a laser, a light emitting diode or other electrical resistance elements. The source 12 is illustrated as being screwed into a socket having appropriate leads 13 extending to the exterior of the cell.

End cap 11 is fitted tightly into the end of porous element 10. An absolute seal is not necessary because porous element 10 itself is gas permeable but the fitting between porous element 10 and end cap 11 is snug enough to prevent leakage of air around the end cap although diffusion of air through the connection is acceptable.

At the other end of porous element 10 there is a second end cap 15 sealed to the porous element 10 in the same manner as end cap 11. The second end cap 15 includes a cavity having set within it an optical filter 16 and a detector 17 which is connected to the exterior of the cell through leads 18. The optical filter 16 is adapted to pass only that portion of the spectrum that is most strongly absorbed by the gas being detected and to filter out other frequencies. Therefore, detector 17 responds strongly to the presence of the gas. The detector may be any device that creates varying electrical responses to corresponding variations in the strength of radiation from the source. The preferred detector to be employed in the device of this invention is a thermopile when measuring infrared radiation.

The cell illustrated in FIG. 1 surrounds a column of air 20 between the source 12 and the detector 17. Changes in the composition of the ambient air surrounding cell 10 cause corresponding changes in the composition of the air in column 20 by diffusion. The pore size of the porous element 10 is selected to provide rapid diffusion of gas while still rejecting dust or other particulate matter in the air. It has been found that average pore sizes of greater than 0.3 microns and between 0.3 to about 100 microns in the element 10 are useful. An average pore size of about 20 microns will permit diffusion of gas through it rapidly enough so that a response to a change in composition of the surrounding air can register on a meter within about 10 seconds after a composition change occurs, and that a full scale indication of a change in composition can be noted within about 30 seconds. The diffusion rate is increased substantially if the device is placed in a flowing air stream or even if it is manually fanned. The sintered element 10 having the above pore size has been found to exclude dust and other particulate matter from air column 20 without building up a filter cake so that its ability to pass gas through the sintered wall remains constant.

The cell illustrated in FIG. 1 may be employed in a system illustrated in FIG. 2. The broken line 10 schematically represents the sintered element 10 illustrated in greater detail in FIG. 1. It is shown in FIG. 2 as enclosing the source 12, the optical filter 16, the detector 17 and gas column 20.

In operation an infrared source is energized through pulsing electric energy delivered through the circuit including leads 13. The infrared passes through gas column 20 and is filtered by optical filter 16 so that only those portions of the infrared spectrum most strongly absorbed by the gas strike detector 17.

Detector 17 produces an electric signal in line 18 that is inversely proportional to the amount of gas being detected. Thus, if carbon dioxide is the gas being detected, the more carbon dioxide present in gas column 20 the weaker will be the infrared radiation striking detector 17. The signal in line 18 is amplified in preamplifier 22 and carried through line 23 to DC restorer 25.

A time base generator 31 is employed to coordinate the entire system. Time base generator 31 is a clock-like device that sends out periodic pulses at regular intervals. Generator 31 causes timed pulses to pass through line 36 which actuate source driver 35 to produce pulses of power to drive infrared source 12 at the time intervals established by generator 31. Generator 31 also controls DC restorer 25 through line 32 and demodulator 27 through line 33 to provide their functions in a pulsed manner that corresponds to the periods during which source 12 is operated.

When source 12 is an incandescent filament it does not function instantaneously. Rather, when source driver 35 provides power to source 12 the filament progressively becomes hotter until a maximum temperature is attained and when power is cut off the filament progressively becomes cooler until it reaches a minimum temperature. Therefore source 12 cycles between a maximum infrared radiation and a minimun infrared radiation. DC restorer 25 establishes the level of infrared radiation at the point of minimum radiation in each cycle and therefore establishes a zero baseline from which all radiation detected by detector 17 can be measured.

The signal from line 18 then passes through line 26 to demodulator 27, the function of which is also pulsed by time base generator 31 via line 33. The demodulator 27 measures the maximum radiation sensed by detector 17 from each pulse of source 12. Combining the signals from restore 25 and demodulator 27 establishes the effect of infrared radiation on detector 17. The signal output 28 of the demodulator 27 is a D.C. voltage which is a function of the concentration of the gas to be measured. This voltage can be applied to a suitable meter 30 which may be calibrated in units of concentration of the gas.

In practice a device embodying this invention is calibrated by being operated with a gas column free of the gas to be analyzed for, or with a stable composition of such gas present, and the signal sent through line 28 to meter 30 therefore indicates a zero reading for purposes of analysis. The meter can be set for zero and any fluctuations in the meter reading when the cell illustrated in FIG. 1 is placed in an environment thought to contain the gas to be analyzed or unusual amounts of the gas will be due to the presence of that gas. Because of the inverse relationship between gas concentration and signal strength a zero reading on meter 30 will indicate the greatest amount of electric energy in line 28 while lesser amounts of electric energy will result from absorption of the infrared radiations by the gas.

The signal output 28 may also be used to drive an adjustable threshold comparator to activate an alarm or a process control means. The alarm may provide a warning of gas concentration that is higher than desired and process control means may operate in a known manner to maintain the concentration of the gas at a selected value.

What is claimed is:

1. A cell for use in an analyzer for a gas comprising:
   a hollow, porous, support element exposed directly to ambient air and enclosing an elongated column of air at ambient pressure into which ambient air may diffuse,
   a source of radiant energy positioned within said porous element at one end of said column and sealed within said porous element,
   a detector for said radiant energy sealed within said porous element and positioned at the end of said column opposite said source and to receive radiation from said source,
   an optical filter positioned between said source and said detector, said optical filter passing only radiation from said source that is strongly absorbed by said gas.

2. The cell of claim 1 wherein the average pore size of said porous element is from about 0.3 microns to about 100 microns.

3. The cell of claim 1 wherein said porous element is porous plastic.

4. The cell of claim 1 wherein said porous element is sintered metal.

5. The cell of claim 4 wherein said porous element is stainless steel.

6. The cell of claim 4 wherein said porous element is sintered bronze.

7. The cell of claim 1 wherein said source of radiant energy is a tungsten filament.

8. The cell of claim 1 wherein said source of radiant energy is a laser.

9. The cell of claim 1 wherein said detector is a thermovoltaic device.

10. An analyzer for a gas comprising: a hollow, porous, support element exposed directly to ambient air and enclosing an elongated column of air at ambient pressure into which ambient air may diffuse,
    a source of radiant energy positioned within said porous element at one end of said column and sealed within said porous element,
    a detector for said radiant energy sealed within said porous element and positioned at the end of said column opposite said source and to receive radiation from said source,
    an optical filter positioned between said source and said detector, said optical filter passing only radiation from said source that is strongly absorbed by said gas,
    means to pulse said source electronically at predetermined intervals,
    means pulsed at the same intervals to detect a minimum signal from said detector,
    means pulsed at the same intervals to detect a maximum signal from said detector, and
    means to indicate the differences between said minimum signal and said maximum signal, said means calibrated to indicate the quantity of said gas in said column.

11. The analyzer of claim 10 having a single means to pulse said source, to pulse said means to detect a minimum signal, and to pulse said means to detect a maximum signal.

12. The analyzer of claim 10 wherein the average pore size of said porous element is from about 0.3 microns to about 100 microns.

13. The analyzer of claim 10 wherein said porous element is sintered metal.

14. The analyzer of claim 13 wherein said porous element is stainless steel.

15. The analyzer of claim 13 wherein said porous element is sintered bronze.

16. The analyzer of claim 10 wherein said porous element is porous plastic.

17. The analyzer of claim 10 wherein said source of radiant energy is a tungsten filament.

18. The analyzer of claim 10 wherein said source of radiant energy is a laser.

19. The analyzer of claim 10 wherein said detector is a thermovoltaic detector.

* * * * *